(12) United States Patent
Faughn

(10) Patent No.: US 11,957,453 B2
(45) Date of Patent: Apr. 16, 2024

(54) DYNAMIC GRIPPING SYSTEM FOR ANTHROPOMETRIC ACQUISITION AND FITMENT FOR WEAPONS AND HAND TOOLS

(71) Applicant: U.S. Army Combat Capabilities Development Command, Army Research Labortary, Adelphi, MD (US)

(72) Inventor: Jim A. Faughn, Glen Arm, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 534 days.

(21) Appl. No.: 17/180,900

(22) Filed: Feb. 22, 2021

(65) Prior Publication Data
US 2022/0265188 A1    Aug. 25, 2022

(51) Int. Cl.
| | |
|---|---|
| *A61B 5/107* | (2006.01) |
| *A61B 5/00* | (2006.01) |
| *A61B 5/22* | (2006.01) |
| *F41A 99/00* | (2006.01) |
| *F41C 23/10* | (2006.01) |
| *F41C 27/00* | (2006.01) |

(52) U.S. Cl.
CPC ............ *A61B 5/1072* (2013.01); *A61B 5/225* (2013.01); *F41A 99/00* (2013.01); *F41C 27/00* (2013.01); *A61B 5/702* (2013.01); *F41C 23/10* (2013.01)

(58) Field of Classification Search
CPC ....... A61B 5/225; A61B 5/1072; A61B 5/702; F41A 99/00; F41C 23/10; F41C 27/00
See application file for complete search history.

(56) References Cited

U.S. PATENT DOCUMENTS

| | | | | |
|---|---|---|---|---|
| 6,804,907 B1 * | 10/2004 | Slobodkin | ............... | F41C 23/14 |
| | | | | 42/74 |
| 6,988,295 B2 * | 1/2006 | Tillim | .................. | B43K 23/004 |
| | | | | 16/110.1 |
| 8,091,264 B2 * | 1/2012 | Goertz | .................... | F41A 19/10 |
| | | | | 42/71.01 |
| 9,310,161 B2 * | 4/2016 | Ermossa | ................. | F41C 23/10 |
| 10,228,208 B2 * | 3/2019 | Galie | ...................... | F41A 19/16 |
| 10,398,417 B2 * | 9/2019 | O'Neil | ................... | A61B 90/06 |
| 2016/0341517 A1 * | 11/2016 | Williams | ............... | B33Y 50/00 |

FOREIGN PATENT DOCUMENTS

| | | | | |
|---|---|---|---|---|
| CH | 688661 A5 * | 12/1997 | ............. | F41A 19/10 |
| CN | 106264543 A * | 1/2017 | | |
| CN | 107343788 A * | 11/2017 | | |
| WO | WO-2015095981 A1 * | 7/2015 | ........... | A61B 5/1075 |

* cited by examiner

*Primary Examiner* — Judy Nguyen
*Assistant Examiner* — James Split
(74) *Attorney, Agent, or Firm* — Alan I. Kalb

(57) ABSTRACT

Various embodiments are directed to systems, apparatus and methods configured for anthropometrics data/measurement acquisition such as for fitment of handguns, hand tools, weapons and the like.

5 Claims, 3 Drawing Sheets

DYNAMIC GRIPPING SYSTEM FOR ANTHROPOMETRIC ACQUISITION AND FITMENT FOR WEAPONS AND HAND TOOLS

GOVERNMENT INTEREST

The invention described herein may be manufactured and used by or for the Government of the United States for all governmental purposes without the payment of any royalty.

FIELD OF THE DISCLOSURE

The present disclosure relates generally to mechanisms for anthropometrics acquisition and, more particularly, to acquiring anthropometrics for fitment of handguns, small arms, weapons, hand tools, and the like.

BACKGROUND

This section is intended to introduce the reader to various aspects of art, which may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

The science of anthropometrics is well established, and there are large databases from which human factors engineers, scientists, designers, doctors and others retrieve anthropometric data for various purposes. The anthropometric data defines the human body very well in static, two-dimensional (2D) scientific terms (e.g., appendage size information) based on strict adherence to well defined and prescribed measurement techniques so as to categorize and classify the human body and its appendages into different size ranges and percentiles.

While useful, such data is not related to the active use of any particular equipment or dynamic function (e.g., gripping a handgun or tool, normal sitting (slumped) posture and so on). For example, in gripping a tool such as a handgun the hand and fingers are required to dynamically function in unison to grip the handgun and concomitantly pull the trigger.

Attempts to measure or estimate trigger pull reach distance using the existing static anthropometric data sets do not accurately reflect the dynamic motion of gripping/using a handgun or tool, which involves many variables that do not effect a static 2D measurement; such as compression of muscle and flesh, joint angles, multiple segments that rotate about each other, multiple segments of differing lengths, effects of tendons, and even the location from which relevant measurements thereof are taken. These and other variables make using static 2D anthropometric data ineffective for characterizing dynamic measurements.

SUMMARY OF THE INVENTION

Various deficiencies in the prior art are addressed below by the disclosed systems, methods and apparatus configured for anthropometrics acquisition such as for fitment of handguns, hand tools, weapons and the like.

One embodiment comprises an anthropometrics acquisition apparatus comprising a forearm cradle, configured to receive a forearm of a user and to provide dynamic support and alignment to a functionally gripping hand of the user; a lower grip, configured to be normally grasped by the middle, ring and little fingers of the functionally gripping hand, and to adjust position with respect to the forearm cradle in response to a positioning of the functionally gripping hand; an upper grip, coupled to a top portion of the lower grip and configured to be grasped by the thumb and trigger finger of the functionally gripping hand, for measuring a curvilinear distance associated with the thumb, thumb crotch, grip to center line to the Digit 2 Distal Phalanx, and trigger finger of the functionally gripping hand; a trigger, adjustably coupled to the grip measuring device via an adjustable Trigger Finger Pull Length Device (TFPLD) and configured to be operated by the trigger finger of the functionally gripping hand, for measuring a trigger finger length of the functionally gripping hand; and a Trigger Finger Pull Force Device (TFPFD), coupled to the trigger, for measuring a dynamic trigger finger pull force of the functionally gripping hand.

In some embodiments, the forearm cradle comprises an elongated base portion having disposed upon an upper surface thereof a plurality of cradles, or the lower grip is slideably engaged with the base portion of the forearm cradle. The TFPLD may be slideably mounted to an upper portion of the grip measuring device and configured to laterally adjust a presentation of the trigger to the trigger finger, and for measuring a lateral offset of the trigger location of the functionally gripping hand.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
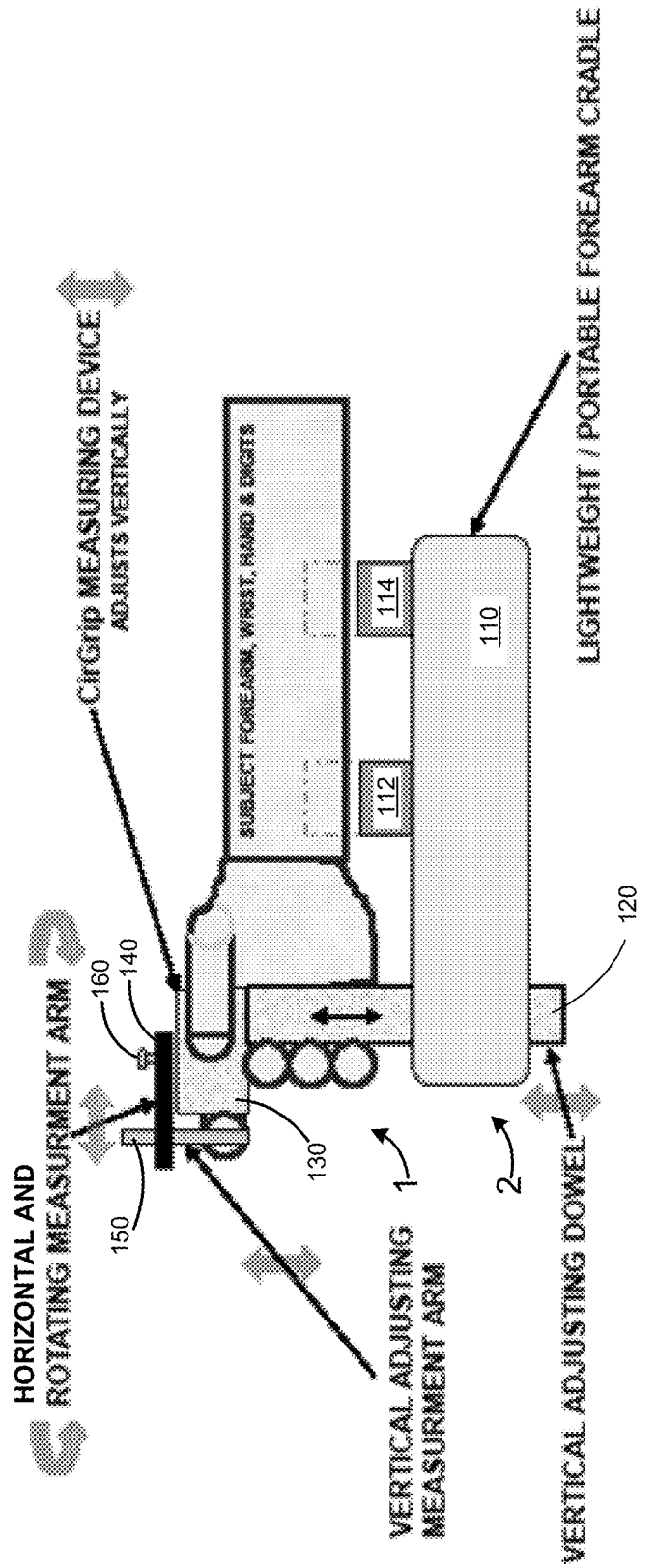
FIG. 1 depicts a weapon fitment apparatus according to an embodiment.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for illustrative purposes to aid the reader in understanding the principles of the invention and the concepts contributed by the inventor to furthering the art and are to be construed as being without limitation to such specifically recited examples and conditions. Additionally, the term, "or," as used herein, refers to a non-exclusive "or", unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the invention is also applicable to various other technical areas or embodiments.

While the various embodiments will be described primarily in terms of a handgun or handgrips pertaining to small arms weapons, the invention is directly relevant to a broad range of hand tools and other equipment. Therefore, for brevity the terms handgun(s) and tool(s) will be used interchangeably with this broader meaning and shall be construed as encompassing the broader applicability of the invention.

Various embodiments are directed to an apparatus configured to generate three-dimensional (3D), dynamic function anthropometric data associated with the use of a particular tool, wherein the generated anthropometric data is suitable for use in improving/replacing existing anthropometric datasets as well as improving individual fitment of tools to a user of the tool. It will be noted that while the embodiments will be primarily described within the context of tools such as handguns, long arms, machine guns and the like, the embodiments also find utility with respect to other tools, and especially other tools having complex dynamic function requirements. Generally speaking, the various embodiments provide 3D anthropometric data associated with the human-machine interface during operation of that tool by a human (i.e., dynamic function).

Various embodiments include methods of capturing and using dynamic 3D anthropometric measurements to enable rapid and accurate man-machine interface fitment, such as the fitment of a personal weapon to a warfighter.

Handgun Embodiments

The man-machine interface of a handgun primarily comprises a grip to enable holding the handgun and a trigger to enable firing of the handgun. The ability of the user to comfortably hold and move the weapon, aim the weapon at a target (e.g., via a sighting mechanism or muscle memory/"feel") and accurately fire the weapon repeatedly on target(s) define the dynamic use of the weapon. For purposes of this discussion, the relevant parameters of the man-machine interface supporting this dynamic use are selected as grip circumference (finger tip to thumb tip circumferential grip distance), grip to trigger distance, grip to center line to the Digit 2 Distal Phalanx, dynamic trigger finger pull length and dynamic trigger finger pull force. Other parameters may also be included. By obtaining "dynamic" (user actively gripping and triggering) versus "static" (non-gripping and non-triggering) anthropometric dimensions related to the human trigger finger length, hand, and grip, the various embodiments optimize proper grip to trigger configurations of weapons so as to enhance shooting performance of virtually all users, irrespective of hand size/shape, finger length/size/shape and so on.

Generally speaking, various embodiments provide systems, apparatus, and methods to dynamically capture and evaluate individual hand measurements such as grip circumference (trigger finger tip to thumb tip circumferential grip distance),grip to trigger distance, grip to center line to the Digit 2 Distal Phalanx, dynamic trigger finger pull length and dynamic trigger finger pull force such that highly accurate fitment of personal weapons may be provided to warfighters.

For purposes of this discussion, the term "Static Trigger Finger Length" is defined as the anthropometric 2D measurement of a trigger finger in a static (i.e., flat and not bent) position, which measures overall length of the trigger finger. This is defined by ANSUR 1988 as the functional length of the second digit calculated as the distance between the tip of the number two digit and the center of rotation of the first metacarpophalangeal joint, approximated by the proximal transverse palm crease.

For purposes of this discussion, the term "Dynamic Trigger Finger Length" as used herein with respect to the various embodiments comprises an anthropometric 3D measurement of a trigger finger in a dynamic (i.e., curved into the position of pulling a trigger) position which measures overall length of the effective trigger finger pull length from the thumb crotch to the trigger.

Various embodiments may be implemented using, illustratively, four instruments or devices as will be discussed below. For purposes of clarity, the four devices will be depicted as separate devices and described as such. However, in various embodiments two or more of the four devices may be combined into a corresponding multiple function device.

The first three of the four instruments/devices operate to accurately measure various grip and trigger parameters of the human hand and digits while dynamically engaged in gripping a handgun or handgrip in preparation for pulling a trigger; the fourth instrument/device obtains measurements from an actual handgun grip or device and/or its corresponding trigger mechanism as would be physically grasped by the user. Briefly, the four instruments/devices comprise:

(1) The "Trigger Finger Pull Length Device" or TFPLD—Accurately measures the proper dynamic trigger finger length of the active gripping hand, with or without gloves, of both left and right handed users, and establishes the correct dynamic thumb crotch landmark on the hand.

(2) The "Circumferential Grip" or CirGrip—Accurately measures the circumferential (perimeter) distance the thumb and trigger finger will encircle while gripping a handgun or similar device, with or with or without gloves of both left and right handed users. It will also measure from the grip to the center line to the Digit 2 Distal Phalanx. The CirGrip may be provided in two configurations/embodiments; namely, (a) a first configuration for use in conjunction with the TFPLD to obtain accurate anthropometric data to establish a scientific data base, and (b) a second configuration comprising a portable, user operated/handheld "fielded version" of the CirGrip sizing gauge for quickly and accurately sizing trigger finger and thumb grip dimensions of human hands for correct selection of anthropometric appropriately sized handgun grip panels, backstraps, palm swells, etc. at the point of issue (military) or purchase (civilian).

(3) The "Trigger Finger Pull Force Device" or TFPFD—Measures the dynamic trigger finger pull force while actively gripping a handgrip, either with or without gloves, of both left and right handed users.

(4) The "Grip Measurement" or GripMes—Measures the actual exterior circumferential (perimeter) linear dimensions of the handgrip/pistol/device that is being gripped, and also obtains the distance from the centerline of the trigger (or switch) to the centerline of the backstrap. The GripMes is useful in characterizing the various options associated with a device such that the correct options are selected for fitment.

The first and second instruments and their subsequent measurements are designed to allow for human hand deformation which occurs when actually gripping a weapon handgrip vs. taking static (non-dynamic) conventional style measurements (Anthropometric instruments) of the hand and fingers. The third instrument is designed to capture the pull force ability of the human trigger finger (possibly other fingers as well) in a manner encompassing all sizes of the human hands, which greatly enhances design specifications and criteria for trigger pull forces on the design of trigger systems in handguns and a multitude of other trigger actuated devices.

It is noted that the proper interface of the trigger and the human is one of the most important variables in being able to accurately fire a weapon in both single and double action trigger pull forces. This information is important in terms of weapon design for a broad range of human hand sizes. Typically the Trigger Pull Force on a single action trigger is much lighter than the Trigger Pull Force required for a double action trigger. A small female (or male) may have difficulty in pulling a heavier double action trigger and maintaining accurate firing of the handgun. By discovering and documenting the various Trigger Pull Forces from a large pool of 5th % to 95th % humans (both male and female), significant data may be generated such as for use in the anthropometric databases, which will allow designers a better understanding of the human capabilities from which to better design weapon systems. The fourth instrument establishes actual physical dimension of an individual's handgun grip, which may be correlated to that of others for study purposes and to individual components for weapons fitment purposes.

Part of the contribution of the inventor is the recognition that superior fitment and anthropometric data may be achieved with (1) multiple measurements of a particular user's hand(s)/finger(s), where (2) each measurement is taken under dynamic gripping/triggering conditions. As such, the various embodiments described herein provide apparatus and methods of multiple dynamic measurements of a particular user's hand(s)/finger(s) to enable accurate fitment of a weapon or tool. The multiple measurements, taken during the dynamic process of actively gripping/triggering a device representing the weapon or tool, provide critical fitment data which, when used to customize sizing and other weapon/tool grip/trigger parameters, enable more precise operation of the weapon/tool by the user. Further, the aggregated fitment data of multiple users may be used to augment anthropometric databases so as to, illustratively, improve the quality of the data representing various segments of the population, thereby improving baseline assumptions about the segments and improving default fitment calculations and initial fitment assumptions (e.g., such as used for weapon or tool manufacturers).

FIG. 1 depicts a weapon fitment apparatus according to an embodiment. Specifically, FIG. 1 depicts a weapon fitment apparatus 100 for dynamic hand and digit fitment-related measurements of a user, such as a warfighter being issued a weapon configured in accordance with such fitment-related measurements.

As shown in FIG. 1, the weapon fitment apparatus 100 comprises a forearm cradle assembly 2 (e.g., a lightweight/portable forearm cradle) comprising an elongated forearm cradle base 110 having disposed upon an upper surface thereof a plurality of cradles 112, 114 for receiving the forearm of a user and providing dynamic co-aligned support to the hand and wrist of the user for functionally gripping an adjustable fitment device 1, illustratively an adjustable weapon fitment device.

The adjustable fitment device 1 and forearm alignment cradle assembly 2 as depicted in FIG. 1 comprise a portable, light weight weapon fitment apparatus 100. In other embodiments, the adjustable fitment device 1 may be used without the forearm cradle assembly 2, such as where an alternate means of supporting and aligning the hand/forearm/wrist of the user when functionally gripping an adjustable fitment device 1.

The adjustable fitment device 1 generally comprises several portions; namely, a lower grip portion, an upper grip portion, and a trigger portion. When properly supported, the middle, ring and little fingers of the functionally gripping hand are positioned to grip the lower grip portion, illustratively a vertical adjusting dowel (VAD) 120 (representing a handgrip), the thumb crotch is positioned against the near side (right side in FIG. 1) of the upper grip portion, illustratively a circumference grip or CirGrip measuring device 130, and the trigger/index finger is positioned at the trigger portion, illustratively just past a vertical adjusting measurement arm (VAMA) 150 (representing a trigger). The VAMA is secured to a horizontal and rotating measurement arm (HARMA) 140, which is rotatably and slidably engaged with the CirGrip measuring device 130 via a pivot/slide mechanism 160.

Trigger Finger Pull Length Device (TFPLD)

The apparatus 100 performs a TFPLD function by dynamically (i.e., during functional gripping) measuring the distance of the human hand from the gripping area (dynamic thumb crotch) of the hand to the center of the trigger/index finger (number 2 digit) Distal Phalanx (correct trigger finger position) while the hand is actively gripping a CirGrip measuring device (e.g., a 1¼" diameter cylinder) either with or without gloves, of both left and right handed users.

Referring to FIG. 1, a user engages the weapon fitment apparatus 100 by placing his or her forearm in the forearm alignment cradle assembly 2 and gripping the lower and upper grip portions as described above. The horizontal and rotating measurement arm (HARMA) 140, which is slidably engaged with the CirGrip measuring device 130 via the pivot/slide mechanism 160, is adjusted until the trigger finger of the user is correctly engaged with the vertical adjusting measurement arm (VAMA) 150 (representing a trigger) to empirically establish thereby the trigger finger pull length of the user.

The Trigger Finger Length is very important to know for various safety reasons; any user must be able to place their Trigger Finger in the correct position on a handgun trigger without actually touching the trigger, especially small handed users. If a user with a short Trigger Finger Length attempts to place their finger on the trigger then the trigger finger may touch/engage with and otherwise move the trigger prematurely. This may result in an un-wanted, premature or accidental discharge of a weapon. The Trigger Finger should be long enough to place itself in the correct position with respect to the trigger without even touching the trigger but just above the surface of the trigger. Only when the user is ready to fire the weapon should the trigger finger ever actually touch and engage with the trigger.

If the short Trigger Finger user is in a "Get Ready to Fire" mode, they must have their finger inside the trigger guard and ready to place it on the trigger but not actually touching the trigger. This may be difficult if the user is struggling to even get their trigger finger safety or correctly near the trigger. Only when the user is ready to fire should the Trigger Finger ever contact the Trigger.

In addition to the safety issue, a user with a short or long Trigger Finger Length may cause them to place the Digit 2 Distal Phalanx (Trigger Finger) centerline in an incorrect position with respect to the trigger. If the centerline of the Trigger Finger and the centerline of the Trigger do not coincide then this will cause the shooter to either push or pull the handgun resulting in less accurate and errant shots on the intended target. If a user rotates the handgun in their grip to better accommodate for a short or long Trigger Finger Length then this will cause misalignment of the handgun centerline with the wrist, hand, and forearm centerlines resulting in an improperly supported and held handgun. This will allow recoil forces mainly to be directed into the muscles of the hand/wrist and not into the bone structure of the wrist, forearm, arm, and body where the recoil force is better absorbed and mitigated—resulting in less accurate control of the handgun during rapid or "double tap" firing of the weapon commonly utilized during combat scenarios.

Trigger Finger Pull Force Device (TFPFD)

The apparatus 100 performs a TFPFD function by dynamically (i.e., during functional gripping) measuring the dynamic trigger finger pull force while actively gripping a handgrip, either with or without gloves, of both left and right handed users. The TFPFD measures the dynamic trigger pull force that the trigger finger (or any other digit) can apply to a trigger (or switch, button, etc.) while gripping a handgrip. This will help to quantify the abilities and parameters of different sized hands, digits, etc. and their ability to apply a constrictive pull (or possibly an expansive) force as would be required for operation of a trigger for a handgun, rifle, drill, paint sprayer, mixer, cyclic control, etc.—anything requiring a combination of gripping and also trigger pull/push activation. This embodiment will be adjustable (both vertically and horizontally to maintain correct trigger finger position with the centerline of the TFPLD) and to concomitantly align its pull force coincident with the centerline of the trigger finger and will be adjustable to place the trigger of the gauge in the exact same spot as previously determined by the TFPLD.

It is noted that the standard 2D static anthropometric definition of the thumb crotch is deemed to be located at the deepest indentation of the space between the first and second digits (thumb and index finger). However, the dynamic thumb crotch may be slightly different in its location on the hand, as it is based on actual gripping functions to locate the "dynamic" centerline of the thumb crotch related back to the wrist, hand, and forearm.

The apparatus 100 simulates the grasping action of a hand that would be gripping the handgrip of a pistol, tool or weapon (such as a handgun or rifle handgrip) while also correctly placing the trigger finger on a trigger, switch, control, etc. that operates the weapon or tool. This gripping action is measured in a linear fashion by the TFPLD. In addition to this linear measure the TFPLD in other embodiments will: also measure the trigger finger pull force generated by the trigger finger (digit 2 phalanges) while the hand is again performing the simulated grip on a pistol handgrip, and measure the circumferential gripping distance (CirGrip) that the trigger finger tip (and also the center line of Digit 2 Distal Phalanx) and thumb tip define around the handgrip of a handgun.

It is noted that multiple measurements of trigger finger pull force may be used to help weapons designers understand the physical ability of different size humans/hands and their effective trigger finger pull force capability, and the CirGrip dimension will also help define proper anthropometric dimensions required to fit the 5th thru 95th percentile male and female populations for external handgun grip circumferences as well as other tools and devices.

The TFPLD and TFPFD functions may be realized/constructed in many ways. One embodiment of the TFPLD comprises a surface block with a centerline inscribed on its upper surface—a forearm cradle(s) is attached to the block's upper surface coincident with the block's centerline—in front of this arm cradle is mounted a vertical 1¼" diameter Delrin dowel on the same centerline—this dowel is moveable up and down to adjust to different hand width sizes and can be secured in position via a knurled head thumb screw located at the front of the TFPLD—near the top of this dowel is mounted a horizontal moveable rod with a right angle downward positioned vertical arm that is normal to the horizontal rod, this rod can slideably extend or retract away from or towards the centerline of the dowel to accommodate different trigger finger pull lengths. This rod/arm can be locked down by a single spade head thumb screw mounted in the top of the dowel to prevent any movement of the measurement rod (during measurement taking) once the correct trigger pull length has been obtained.

In various embodiments, some or all components of the TFPLD may be stowed inside the TFPLD so it is totally portable and avoids damage or loss during shipmen, transport, handling, etc. In various embodiments, the moveable arm/rod (which can be measured with a caliper) may be replaced with a digital readout measurement device. The use of a caliper reduces cost and complexity of the device, and allows any existing anthropometric measuring tools/calipers the ability to also use the TFPLD without any modification or additional needed tool(s) other than standard anthropometric or mechanical/digital calipers. An embodiment with a digital trigger pull force measurement feature may also be an additional organic attachment (e.g., stowed onboard the TFPLD), use a device that will accept a measuring tool, or similar pull/push force tool set-up.

In various embodiments, the TFPLD and CirGrip may be configured to accommodate the actual devices; grips, backstraps, panels, palm swells and the like being measured or designed for specific weapons, tools, handguns to obtain exact measurements while replicating the weapons actual grip devices and the dynamic human's anthropometric gripping dimensions.

In various embodiments, the 1¼" diameter Delrin (or other material) rod that forms the gripping device may be configured to accept different grips, panels, backstraps, palm swells, etc. to mimic the exact configuration of a specific handgun, weapon, tool, etc. if desired. This allows further uses for the TFPLD aside from only gathering scientific anthropometric data, it will also allow weapon designers and manufacturers the ability to evaluate their gripping systems and designs on a common platform that can be used across the board for all weapon designers to measure the dynamic gripping functions in a standardized method. In this manner, all dimensions related to gripping tools can be relatable to each other by sharing a common datum or starting point, this allows sharing and comparing data across different platforms with a common measurement system that is repeatable and relatable to each other. This will also allow handgun gripping requirements of future weapon system's design to be more accurately explained and defined in the requirements documents to ensure a proper range of gripping dimensions is established to accurately accommodate the $5^{th}$ thru 95% tile male and female populations.

In various embodiments, the vertical Delrin gripping rod itself can be modified to accept various devices in many ways; flat sides on the rod to mimic the mounting configuration of weapon frames for mounting of grips, the shape of the rod can be modified to accept "grip modules" that would slip down over the modified shaft and time the assemblies in the correct position, it could accept shims to increase or decrease the different dimensions associated with obtaining the best gripping parameters, the rod could be constructed to be expanding or contracting to provide an unlimited and wide range of adjustments to validate different gripping dimensions, configurations, etc.

Generally speaking, the TFPLD, CirGrip and related devices may be configured and modified to accept gripping accessories/devices that can be positioned onto the rod for evaluations based on measuring the anthropometric range of human hand and finger sizes for design of equipment and to validate adherence to accommodation of 5th % female to 95th % male population requirements.

Circumferential Grip (CirGrip)

The CirGrip (130) function of the apparatus 100 of FIG. 1 accurately measures the curvilinear perimeter surface distance (circumferentially) that a trigger finger, thumb crotch, and thumb can actually grasp around while concomitantly gripping the handle of a weapon or tool. In one embodiment, the CirGrip is used in the TFPLD as shown. In other embodiments, the CirGrip is provided as a stand-alone, portable handheld unit.

Generally speaking the CirGrip may be used to obtain a measurement for both Left and Right handed users (the extreme ends (the tips) of the thumb and index finger), as well as a measurement of the distance to a centerline of the Digit 2 Distal Phalanx (correct trigger finger position) so that this critical linear dimension is also discovered. This dimension is critical because it defines the correct or incorrect placement of the trigger finger in relation to the actual centerline position of the handgun's trigger. This dimension is also critical when placing the trigger finger on a trigger to fire a weapon correctly, safely and accurately. In other applications, such as when the trigger finger is simply activating a switch, while this dimension may not be as critical, it should still be placed anthropometrically and ergonomically correct to ensure a comfortable and proper grip position and to eliminate fatigue and stresses on the hand/trigger finger.

Various embodiments of the trigger portion of the fitment assembly may be provided. The various embodiments generally provide a user-employed, portable device made to quickly and accurately measure the warfighters trigger finger length, digit 2 distal phalanx length and centerline, and thumb gripping (circumferential) lengths in the field. These lengths will be compared to a validated data sheet of handgun and grip sizes to select the best combination of grip panels/backstraps/devices/etc. so the warfighter will get the best ergonomically correct grip configuration possible on the handgun in the shortest period of time that accurately accommodates their particular hand/trigger finger sizes.

Figure 2:
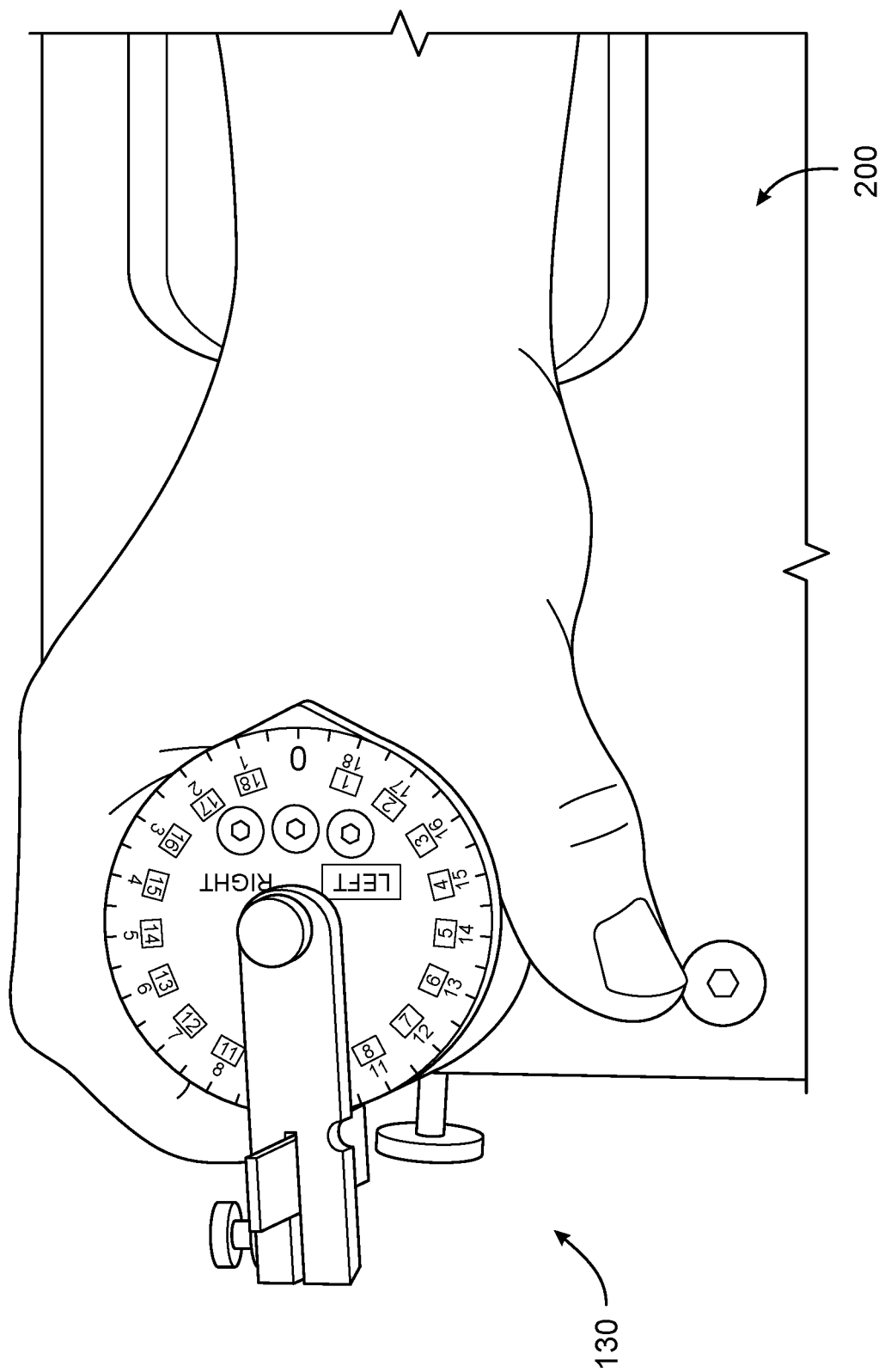
FIG. 2 depicts a circumferential grip measurement device according to an embodiment and suitable for use in the apparatus of FIG. 1.

FIG. 2 depicts a circumferential grip measurement device according to an embodiment and suitable for use in the apparatus of FIG. 1. Specifically, the circumferential grip measurement device 130 of FIG. 2 may be used to measure dynamic (hand in gripping mode) circumferential grip distance for both the thumb and trigger finger—it also will measure the circumferential distance to the centerline of the Digit 2 Distal Phalanx link in this circumferential mode. It comprises, illustratively, a 1¼" diameter Delrin dowel that the three digits (3, 4, & 5 below the trigger finger) grip around to simulate a handgun grip and above that is mounted a 2⅜" diameter cylinder around which the thumb and trigger finger grip. The 19-20 cm (roughly a 2⅜" diameter) cylinder is sized to accommodate both a 95th percentile male (or larger), yet still maintain a comfortable grip for smaller handed subjects (e.g., $5^{th}$ percentile female).

The user or subject grips the lower grip (smaller diameter dowel) with the three digits (numbers 3, 4, & 5) as shown in FIG. 1, and places the thumb crotch in the proper position with the CirGrip indicator tip at the "0" marking of the scale and then places the thumb and trigger finger around the larger cylinder. The measurement cylinder has a zero setting indicator which is coincident with the centerline of the TFPLD and thumb crotch—thus the thumb crotch can be accurately identified and marked onto the subjects hand when the CirGrip is positioned with either the TFPLD or in a standalone version. The CirGrip can be used independently of the TFPLD and that is the purpose of instrument 2B—it also properly aligns the thumb crotch, wrist, and forearm to ensure proper anthropometric alignment but without the larger base block, it uses a smaller portable forearm cradle assembly that could even be a minimalistic wire frame that supports the twin cradles.

On top of the large cylinder is a circular scale with two rows of numerals on it graduated in centimeters—one reads the data for a right handed person (numerals not in a "box") and the other row of numerals (in the "box") read the measurement for a left handed subject, from "0" to "19" cm, as is provided via the right hand and left hand labeling convention on the top of the scale. There is a measurement bar 140 which rotates 360 degrees slightly above the measurement scale and pivots about the center of the large cylinder, it has a vertical moveable right angle appendage (arm) 150 which is positioned over the side of the cylinder which is used to measure the extreme length of both the thumb tip and trigger finger tip by rotating it around until it just touches the tip of either digit—at this point the measurement will be read from the appropriate scale on top of the cylinder thru the viewing window on the rotating measurement bar (not shown in the photo). The appendage/arm that measures the tips of the digits is also moveable vertically within the rotatable arm and when it is moved upwards and locked into position and rotated to the centerline of digit 2 distal phalanx, it will also read the centerline of the Digit 2 Distal Phalanx link circumferential grip distance—the pointed tip of this bar is coincident with the centerline of the bar and again the number read off the scale will define the dynamic TFGL (Trigger Finger Grip Length).

These anthropometric tools allow anthropometrists and designers to gather dynamic data used for gripping of tools and items that need a trigger finger to operate the said tool; handguns, rifles with handgrips, power tools, paint sprayers, etc. In the case of the handguns, once a large enough "N" (data pool of human subjects) has been measured and the data analyzed and tabulated, it will then be possible to produce a simplified "field" gauge to accurately size warfighters hands/trigger finger lengths when being issued small arms and handguns—they will be able to grip the CirGrip and quickly determine what size of backstrap, side grip panels, palm swells, etc. should be applied to the handgrip of their issued handgun (or frame size) to accommodate their particular hand, trigger finger length and grip size. This will ensure the warfighter is getting a properly sized/configured weapon so they can efficiently, safely and accurately operate the weapon. In addition, this will speed up the issuing of handguns and expedite determining the correct size of anthropometric panels needed, as most weapons are issued with the entire suite of replaceable panels and it is up to the user to select the proper panels according to their hand size—this means that they must install and try each panel until they select the correct one(s)—now they can be rapidly "sized" and quickly issued with only the panel(s) needed to accommodate the warfighter by using the "field" gauge to determine the correct anthropometric human size and determine the combination of correct panel(s) to properly fit them. This will save money by only issuing the correct sized panel(s) to the users.

Grip Measurement (GripMes)

The grip measurement (GripMes) function provides an accurate measurement of the 360° curvilinear surface perimeter distance from the thumb crotch of the handgun backstrap around to the centerline of the trigger face. This measurement defines the entire circumferential surface distance (perimeter) specific to each model of handgun and associated grip panels. It is useful in measuring all the different distances based on what combination of specific grip panels, backstraps, palm swells, frame sizes and the like that are attached/installed on the handgrip of the handgun. This data establishes a data base against which the users hand gripping measurements are compared to determine the correct configuration of grip panels, backstraps, palm swells, frame sizes, etc. required to properly fit the individual user when using the fielded 2B CirGrip device. The various embodiments may also be used to measure the circumferential distance (perimeter) around only the grip of the handgun as well, in fact, it can be used to measure surface perimeters of any handgrip or device to determine the total gripping surface linear dimension. This measurement will be used in determining the correct grip devices (panels, backstraps, palm swells, frames, etc.) and size combinations needed to accommodate the 5th through 95th % tile male and female anthropometric hand and trigger finger length sizes for correct handgun sizing to human hands. This measurement is required to cross-reference and compare the CirGrip dimension to the actual measurement of the handgun grip itself (GripMes).

Figure 3:
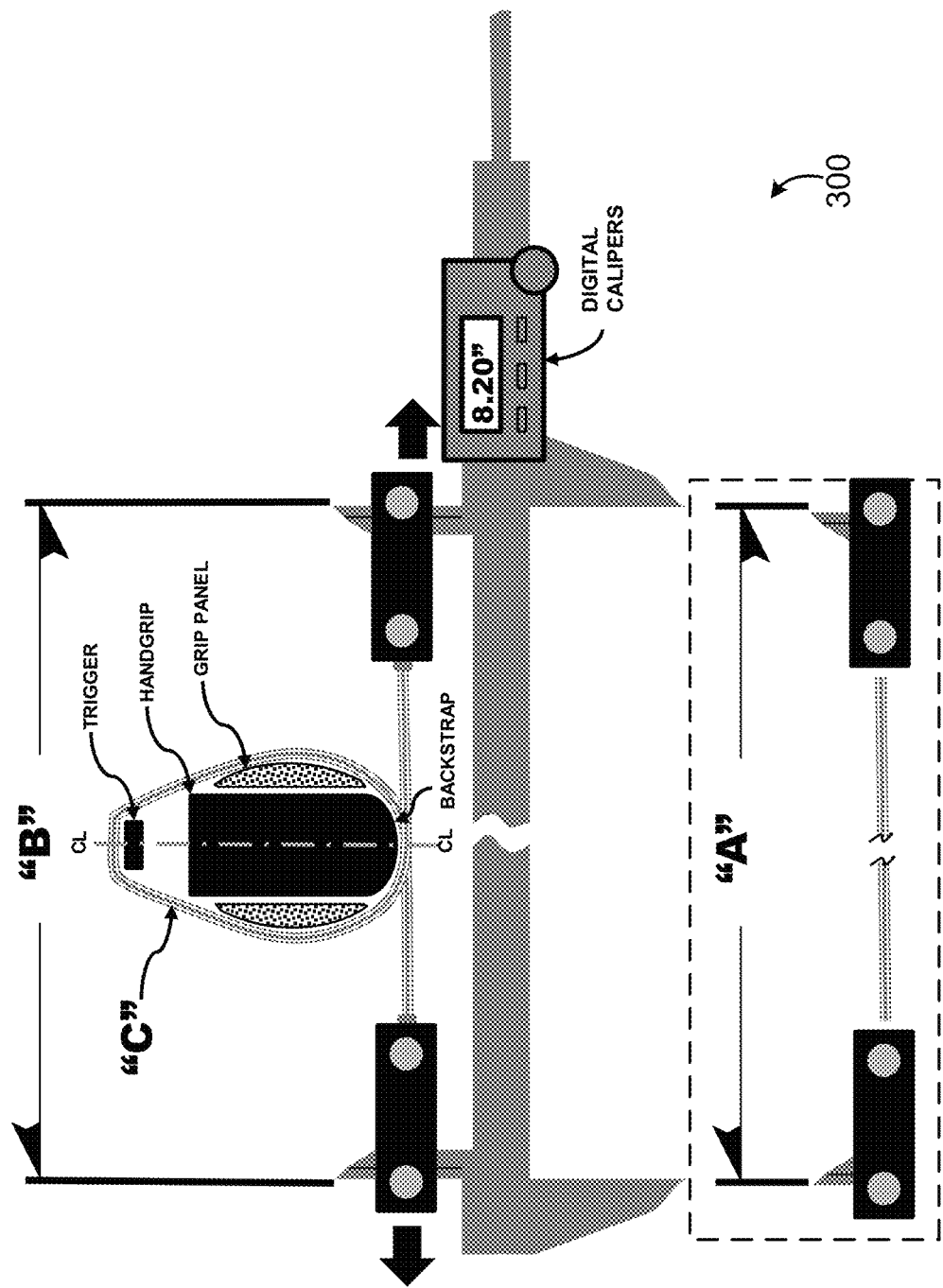
FIG. 3 depicts a grip measuring device suitable for use with the various embodiments.

FIG. 3 depicts a grip measuring device suitable for use with the various embodiments. Specifically, the grip measurement device (GripMes) 300 of FIG. 3 is designed to accurately measure the circumferential linear (perimeter) distance that a hand would need to negotiate when gripping a handgun grip and placing the trigger finger correctly on the centerline of the weapons trigger.

FIG. 3 depicts a top down view of a pistol handgrip and a trigger, wherein the handgrip is further configured with a pair of grip panels and a backstrap. The total gripping circumference ("C") may be defined by, illustratively, a cable wrapped or routed around the handgrip and trigger. An example of FIG. 3, a digital caliper is used to extend a cable, illustratively a 15 inch cable assembly (length "A"). When the cable assembly is wrapped or routed around the handgrip and trigger, the resulting measurement of, illustratively, 8.2 inches (length "B") means that the gripping circumference "C" is 6.8 inches for a pistol handgrip and trigger configured as described herein.

Each pistol, handgun, tool or other grip-configurable device to which fitment may be made has associated with it a respective gripping circumference. In the case of a pistol, various sizes of panels and/or backstrap's may be provided by the manufacturer (e.g., small, medium, large). As such, the gripping circumference of the pistol (or other device) may be adjusted to suit the fitment information derived by the apparatus 100 of FIG. 1 as described above.

Thus, in one embodiment an overall known length (e.g., 15"+/−0.002") is defined between the center adapters/devices located at each end of the cable. In this embodiment, the cable may comprise a small diameter vinyl coated wire (to prevent damage to the firearm) 0.014" in diameter and 15 inches long (in total) with two centering adapter devices, one each attached at opposite ends of the cable. The attachment devices each have two clevis pins in them, one runs through the circular connector opening that attaches to the end of the wire cable and the other clevis pin allows a single point of contact with the measuring face of the electronic caliper arm.

To use this measuring device, one center adapter is passed through the trigger guard of the handgun and the wire cable then rests on the face of the trigger, each adapter is then brought to the rear of the handgrip and crossed over each other to form a single loop in the cable around the backstrap of the handgun grip and then each adapter end is positioned on the respective leg of a digital caliper—as the arms of the caliper slide apart the loop constricts and becomes smaller around the handgun grip.

The interior center adapter's first clevis pin attaches to the cable's swivel connector (mounted at the end of the cable) and is then held in place via the removable clevis pin—the clevis pin runs through the connector's opening inside diameter—this allows the cable to freely rotate and find true concentric centerlines coincident with each other during the measurement process. Within the adapter is also a pocket designed to fit loosely over the jaws of an electronic caliper—there is a second clevis pin inside this pocket that interfaces with a single point of contact against the face on the edge of the caliper's internal jaw so as to not induce any parallax or stiction on the measuring tool—it is free to move and rotate to find exact centers coincident with the cables and makes contact at only one point for accurate and repeatable measurements.

The tool may be used in the following manner: the center adapter at one end of the cable is inserted through the trigger guard of the handgun in front of the trigger, this places the cable onto the face of the trigger and then both adapters are brought to the rear of the handgun grip beneath the beavertail area on the grips backstrap area (where the thumb crotch would interface with the grip)—here they are crossed over each other and then each of the adapter connectors are attached to one of the opposing slide jaws of the caliper—so the cable now crosses over itself at the backstrap area of the handgun grip below the beavertail and the adapter ends are then attached to the sliding jaws of the digital caliper—as the jaws of the caliper are opened (spread apart) the cable begins to constrict and close on itself at the cross over point on the back strap—when all of the cable is in contact with the circumferential surface (perimeter) around the handgun grips and the face of the trigger; and the cable forms a straight line between the ends of the caliper and is also parallel with the main caliper slide beam, the measurement can be made. Thus, the cable will center itself and establish the direct two point (shortest) circumferential distance between the trigger and the thumb crotch of the weapons backstrap as well as the circumferential distance around the grips (i.e., the circumferential grip distance). This is the smallest distance around the entire perimeter of the handgun grip concerning trigger pull. When you subtract the caliper readout number from 15" (known distance of the GripMes) it will provide the exact total exterior perimeter distance from the beavertail thumb crotch area around to the centerline of the trigger (both sides)—and this is the total perimeter measurement. Once the perimeter value has been defined then it can be divided by two to determine the Trigger Reach Distance (circumferential) of that particular firearm/handgun/tool for one side of the grip. This is the shortest perimeter distance on one side of the handgun between both the centerlines of the trigger and the thumb crotch area on the backstrap area of the handgun.

It is noted that the cable must be allowed to form a straight line with itself near the beavertail or backstrap of the weapon (parallel with the main slide beam of the caliper)—this automatically finds the center point of the cable that is not in contact with the grip of the handgun—this portion of the cable is unused (not in contact with the grips in any way) thus when you subtract the unused cable reading on the calipers from the known 15 inches the entire circumferential grip distance is determined. Note: the measurement is established from the Outside Diameter of the cable as it interfaces with the handgun surface and not the centerline of the cable—however, the OD of the cable that contacts the grip surface is what limits the measurable loops distance—so, the device is actually measuring the exact circumferential grip distance.

Most military issue handguns use straight symmetrical grip panels on the handgun and if they are symmetric then this measurement is correct, if there are no other aberrations on the handgrip, i.e. thumb rests, finger grooves, etc. If however, either one or both of the grip panels has a thumb rest, swell or different configuration that is not symmetric to both grip panels then the measurement will not be symmetrically correct. In this case the non-symmetric panel can be removed and another standard panel be put in place for the measurement to be taken. If both panels are removed then the Trigger Reach Dimension (TRD) can be determined but the Circumferential Distance (CD) cannot. Grip panels must be in place in order to measure the total CD of the grip. TRD is defined as the shortest inline distance between the face of the trigger and the surface of the backstrap—without any contour of grips considered.

In another embodiment to measure non-symmetric grips or configurations that cannot be made symmetric on the handgun a modified system will be used. In this instance, the measuring device is basically the same with slight modifications/additions. In order to properly measure the circumferential distances (CD) around the handgun grips each half of the grip must be measured independently of each other. This device has a center positioning clamp attached to the cable's midpoint which is placed over the trigger and tightened down to grip it. This holds the measuring cable in place on the trigger's face and also places the center line of the cable (mid-point from ends of cable) congruent with the center line of the trigger. The cable is locked into this position and will not move once it is clamped to the trigger. Near the cable ends (on either side of the cable) are sliding and locking ferrules that are positioned and contained on the cable, these are moveable against slight resistance and are used to locate and mark the center point of the crossed cables at the backstrap area of the handgun where the measuring cables cross each other. Once the cables are crossed and their common center point has been found, the sliding ferrules are slid into the exact center point to mark it—they are then secured in place by a small spring clamp or similar means to ensure their positions on the cable do not move or change. The overall reading of the circumferential distance is determined in the previous manner—next, the CD system is removed from the handgun and laid flat on a surface and held taught for the secondary measurement. One side of the measuring cable is measured with the calipers from the center of the trigger clamp (add the known distance to the center of the clamp from the edge of the clamp) to the sliding ferrule's edge that was positioned at the centerline of the crossed cables—this provides the exact CD measurement of one side of the handgrip. This measurement can then be subtracted from the overall dimension previously determined to discover the exact CD of the other half of the handgun grip. This provides exact CD measurements for both sides of the non-symmetric gripped handgun. This will be useful in selecting and applying the correct grip panels for the trigger finger side and the thumb side of the handgrips when non-symmetric grips are employed. This allows for different sizes of grip panels to be determined for the best anthropometric fit of the human hand against the handgun grip.

Various modifications may be made to the systems, methods, apparatus, mechanisms, techniques and portions thereof described herein with respect to the various figures, such modifications being contemplated as being within the scope of the invention. For example, while a specific order of steps or arrangement of functional elements is presented in the various embodiments described herein, various other orders/arrangements of steps or functional elements may be utilized within the context of the various embodiments. Further, while modifications to embodiments may be discussed individually, various embodiments may use multiple modifications contemporaneously or in sequence, compound modifications and the like.

Although various embodiments which incorporate the teachings of the present invention have been shown and described in detail herein, those skilled in the art can readily devise many other varied embodiments that still incorporate these teachings. Thus, while the foregoing is directed to various embodiments of the present invention, other and further embodiments of the invention may be devised without departing from the basic scope thereof. As such, the appropriate scope of the invention is to be determined according to the claims.

What is claimed is:

1. A method of functional grip fitment, comprising:
   receiving a user forearm in a forearm cradle configured to provide dynamic support and alignment thereto;
   receiving a first portion of a functionally gripping user hand at a lower grip operatively aligned with the forearm cradle and configured to be normally grasped by a middle finger, ring finger, and little finger of the functionally gripping hand, and configured to adjust position with respect to the forearm cradle in response to a positioning of the functionally gripping hand;

receiving a second portion of the functionally gripping hand at an upper grip operatively coupled to a top portion of the lower grip and configured to be normally grasped by a thumb and trigger finger of the functionally gripping hand, and configured to determine via a curvilinear surface a circumferential grip distance associated with the thumb tip, thumb crotch, centerline of trigger finger distal phalanx and trigger fingertip of the functionally gripping hand;

receiving the trigger finger of the functionally gripping hand at a trigger adjustably coupled to the upper grip, and configured to determine via adjustment thereof a trigger finger length of the functionally gripping hand;

determining, in response to a dynamic trigger finger pull force exerted on the trigger by the trigger finger of the functionally gripping hand, a trigger finger pull force of the functionally gripping hand; and determining a handgrip fitment using the determined circumferential grip distance, trigger finger length, and trigger finger pull force of the functionally gripping hand.

2. The method of claim 1, wherein the determined circumferential grip distance defines a backstrap and grip panels of a weapon fitted to the user.

3. The method of claim 1, further comprising: using a plurality of circumferential grip distances that are defined by a respective backstrap size and grip panel size to fit an associated weapon.

4. The method of claim 1, further comprising: using the determined circumferential grip distance, trigger finger length, and trigger finger pull force to fit a weapon or tool to the functionally gripping hand.

5. The method of claim 1, further comprising: using the determined circumferential grip distance, trigger finger length, and trigger finger pull force to update data in an anthropometric database.

\* \* \* \* \*